US009927347B1

(12) United States Patent
LoPresti et al.

(10) Patent No.: US 9,927,347 B1
(45) Date of Patent: Mar. 27, 2018

(54) PNEUMATIC RAM ROAD SURFACE COEFFICIENT OF FRICTION MEASURING DEVICE AND METHOD

(71) Applicant: State of California Department of Transportation, Sacramento, CA (US)

(72) Inventors: Thomas LoPresti, Placerville, CA (US); Joseph F. Peterson, Marysville, CA (US)

( * ) Notice: Subject to any disclaimer, the term of this patent is extended or adjusted under 35 U.S.C. 154(b) by 137 days.

(21) Appl. No.: 15/143,591

(22) Filed: May 1, 2016

Related U.S. Application Data

(60) Provisional application No. 62/155,364, filed on Apr. 30, 2015.

(51) Int. Cl.
*G01N 19/02* (2006.01)

(52) U.S. Cl.
CPC .................. *G01N 19/02* (2013.01)

(58) Field of Classification Search
CPC .. B08B 1/02; B26D 1/36; B26D 3/282; B26D 7/1863; B29C 63/0013; G01N 19/02
USPC .................... 73/9, 28.06, 128, 146
See application file for complete search history.

(56) References Cited

U.S. PATENT DOCUMENTS

| 4,594,878 | A | * | 6/1986 | Abe ................. G01N 19/02 73/146 |
| 4,947,332 | A | * | 8/1990 | Ghoneim .............. B60T 8/172 180/197 |
| 5,229,955 | A | * | 7/1993 | Nishiwaki .......... B60G 17/0182 180/415 |
| 5,385,393 | A | * | 1/1995 | Tanaka ................ B60T 8/1706 303/150 |
| 6,203,121 | B1 | * | 3/2001 | Kato ....................... B60T 8/172 188/181 A |
| 7,751,961 | B2 | * | 7/2010 | Salman .................. B60T 8/172 180/197 |
| 8,682,599 | B2 | * | 3/2014 | Shiozawa ............... B60T 8/172 303/149 |
| 2001/0006002 | A1 | * | 7/2001 | Ueda ..................... B60T 8/172 73/9 |
| 2004/0144167 | A1 | * | 7/2004 | Halliday ................ G01N 19/02 73/146 |
| 2006/0144121 | A1 | * | 7/2006 | Neubert ................. G01N 19/02 73/7 |
| 2010/0192665 | A1 | * | 8/2010 | Olsen ..................... G01N 19/02 73/9 |

* cited by examiner

*Primary Examiner* — Eric S McCall
*Assistant Examiner* — Mohammed E Keramet-Amircolai
(74) *Attorney, Agent, or Firm* — Craig A. Simmermon

(57) ABSTRACT

Pneumatic ram road surface coefficient of friction measuring device is a stationary device that measures the coefficient of friction of a particular spot on a road surface using a known and precise amount of resistance force supplied from a pneumatic ram and a calibration valve. Pneumatic ram road surface coefficient of friction measuring device comprises a testing tire and wheel mounted to a carriage plate that is slideably attached to a framework that pivots around the front end of the framework and is supported by a jack mechanism at the rear end. Pneumatic ram provides resistance to the sliding action of the carriage plate that may be varied using the calibration valve. Pneumatic ram road surface coefficient of friction measuring device further comprises a sliding gauge indicator and coefficient of friction graduations that provide the coefficient of friction reading.

8 Claims, 9 Drawing Sheets

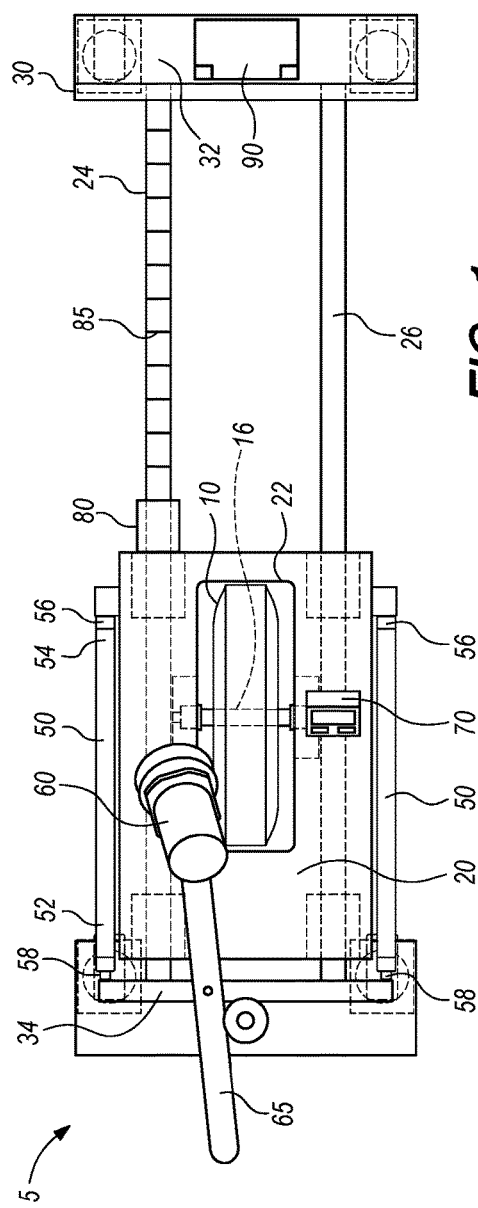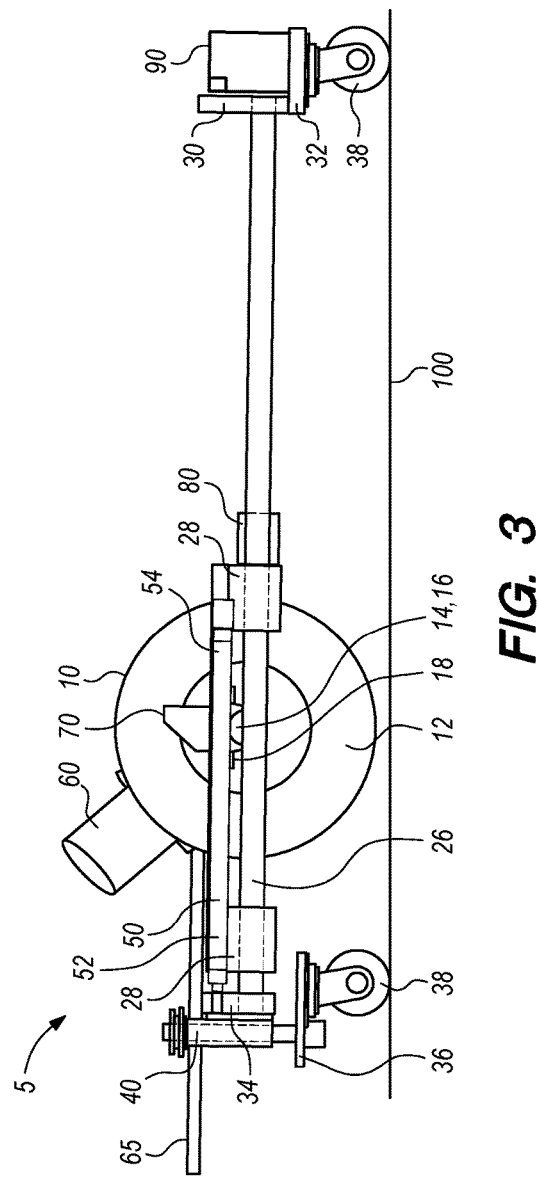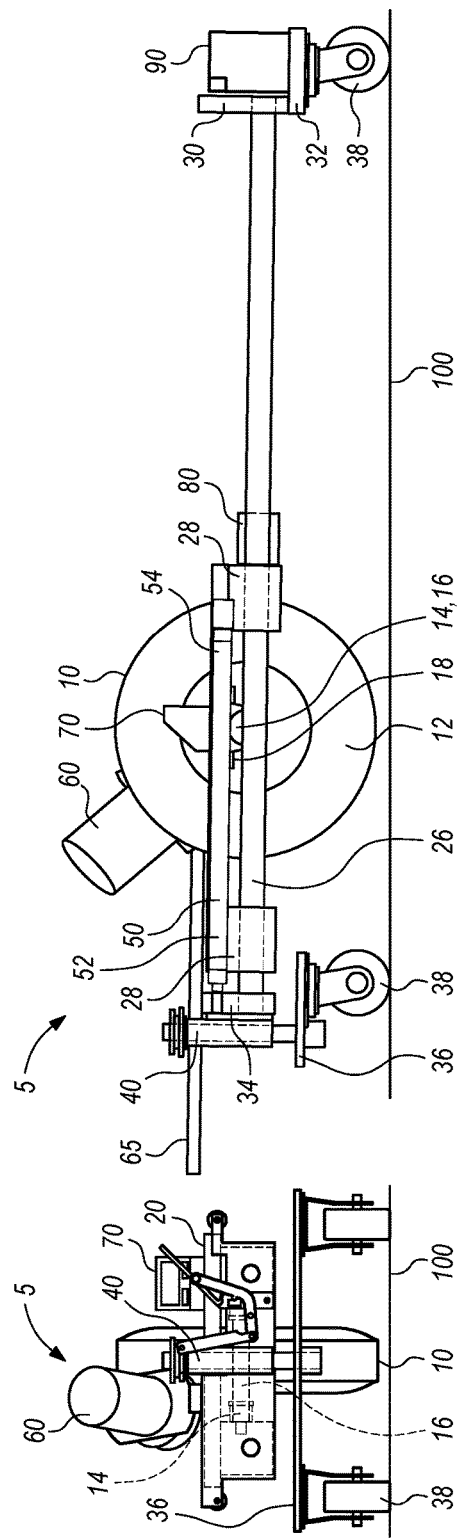
FIG. 1
FIG. 3
FIG. 2

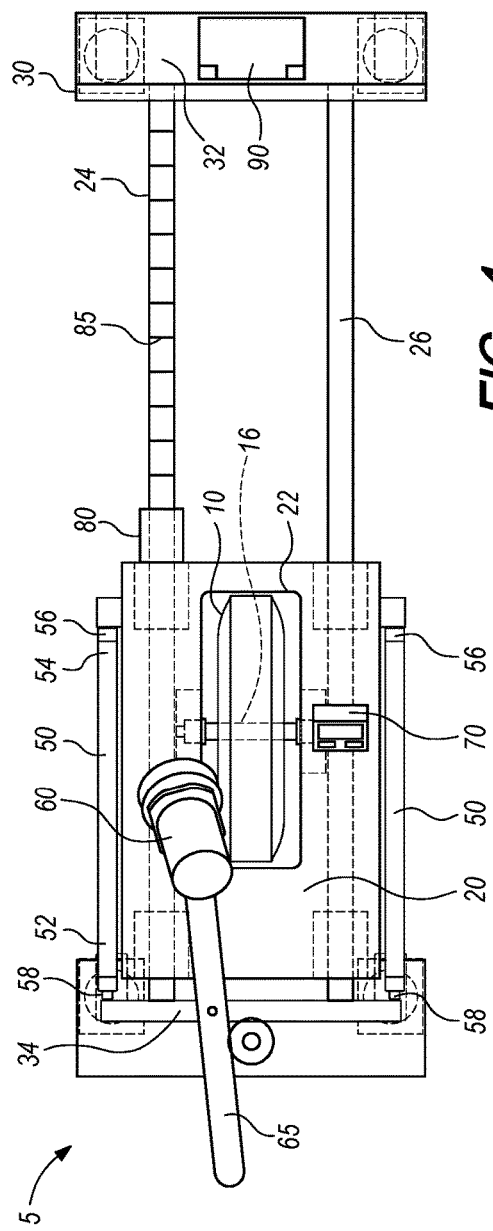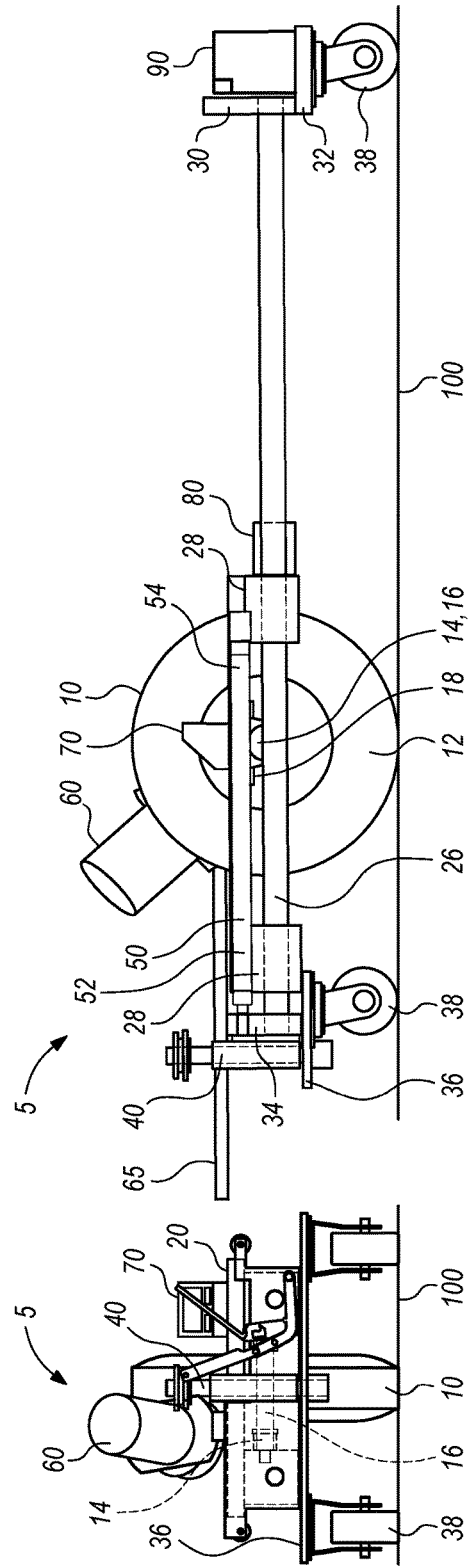

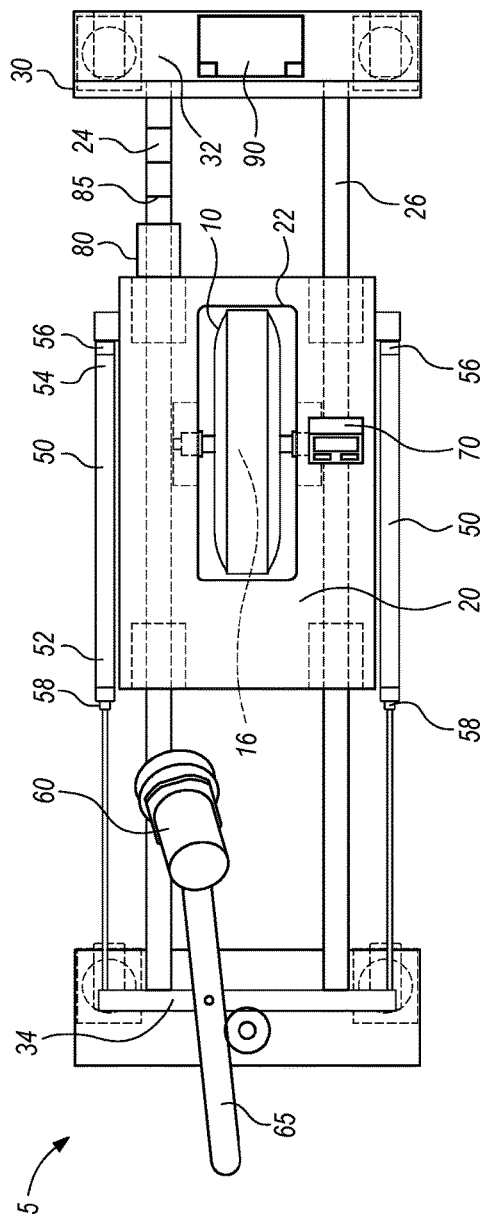
FIG. 7
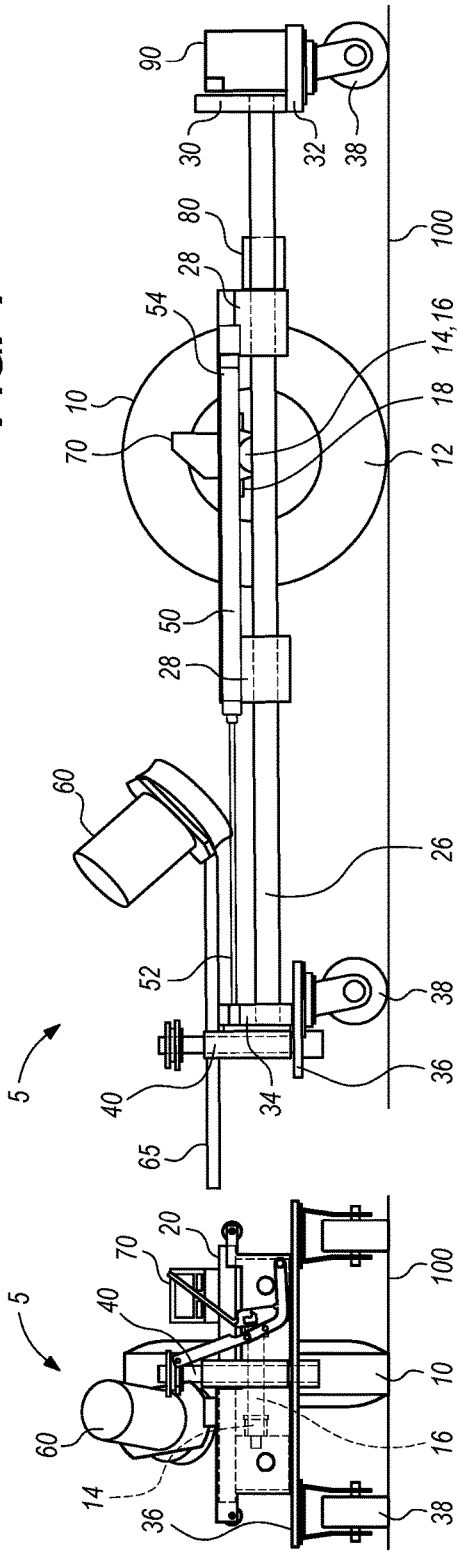
FIG. 9
FIG. 8

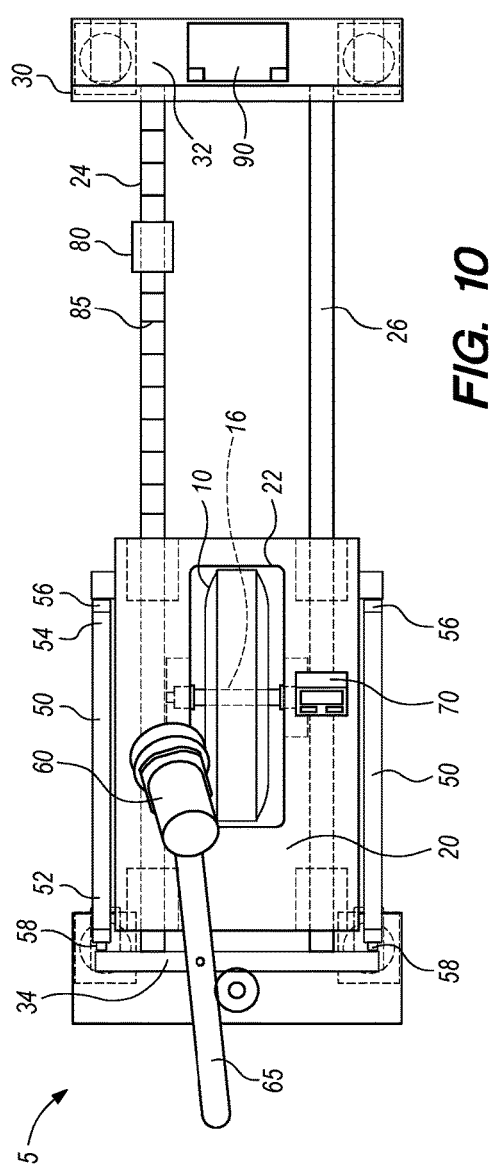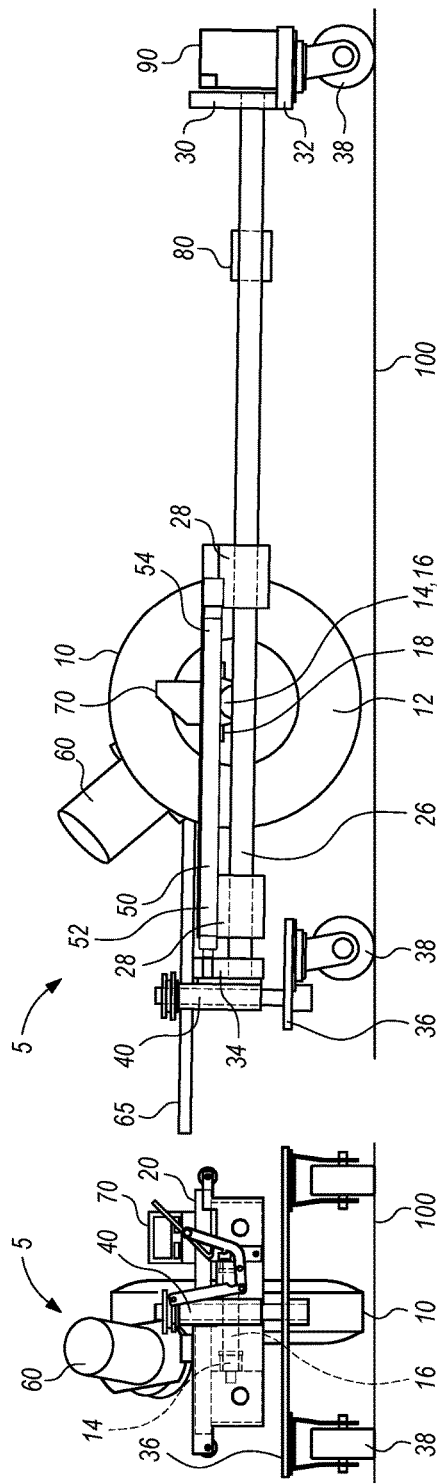
FIG. 10
FIG. 12
FIG. 11

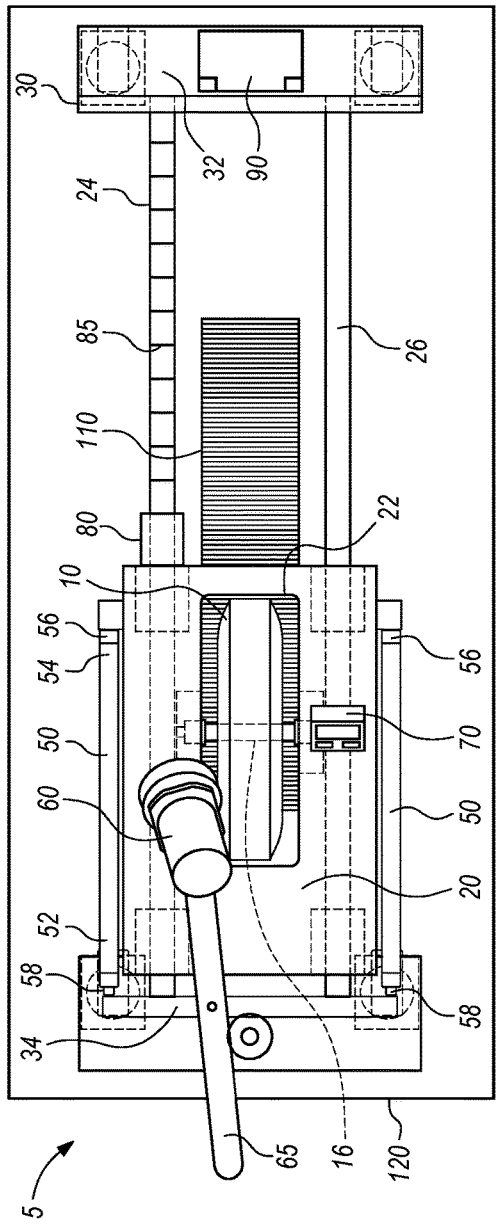
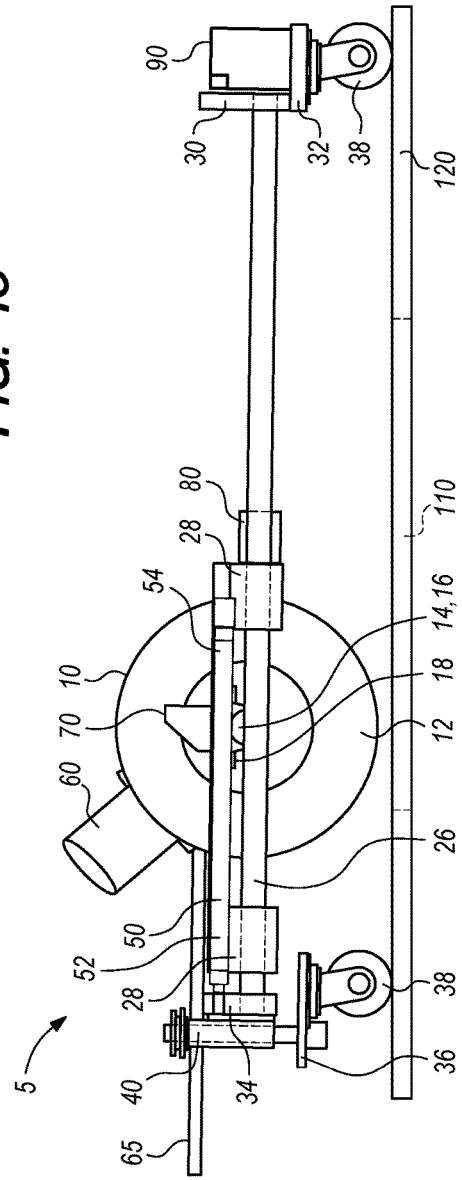
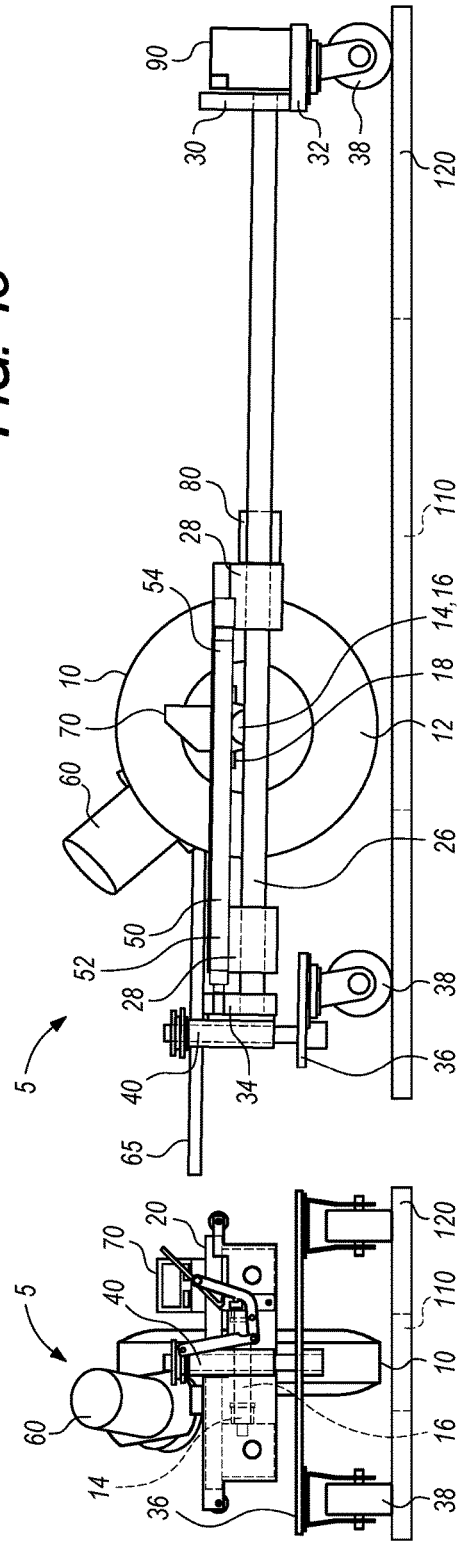
FIG. 13
FIG. 14
FIG. 15

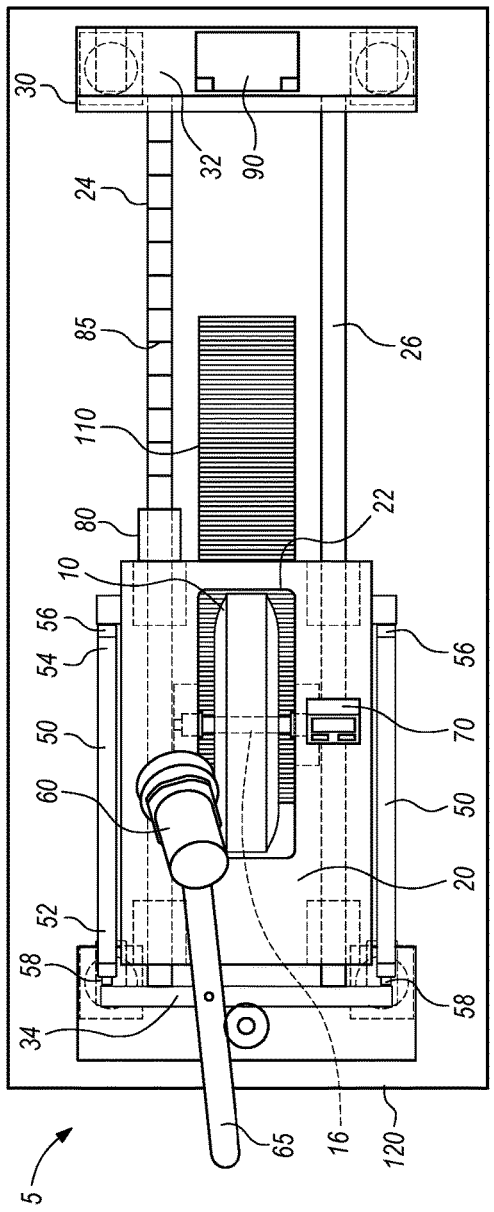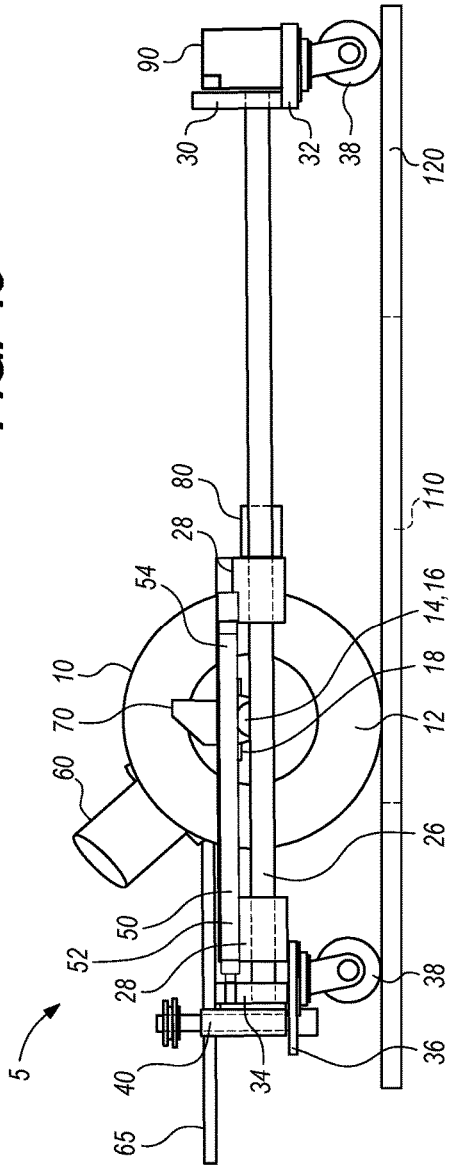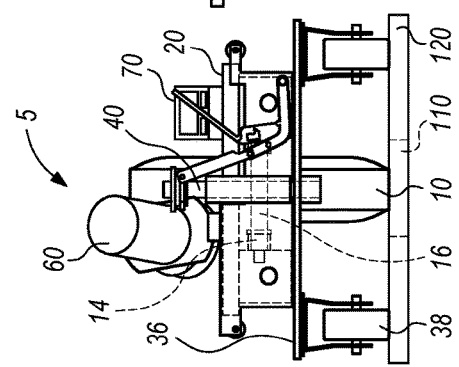

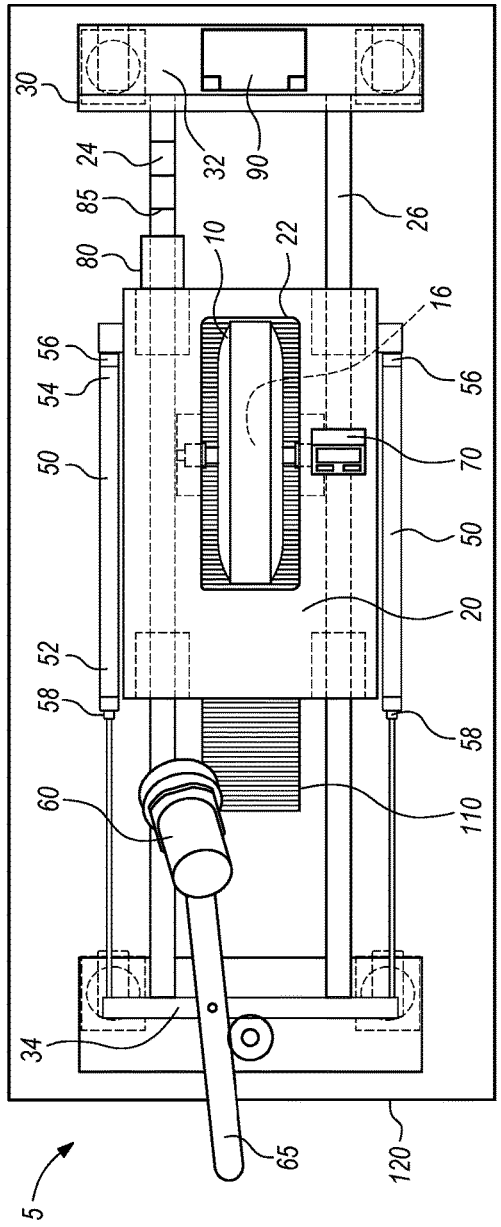
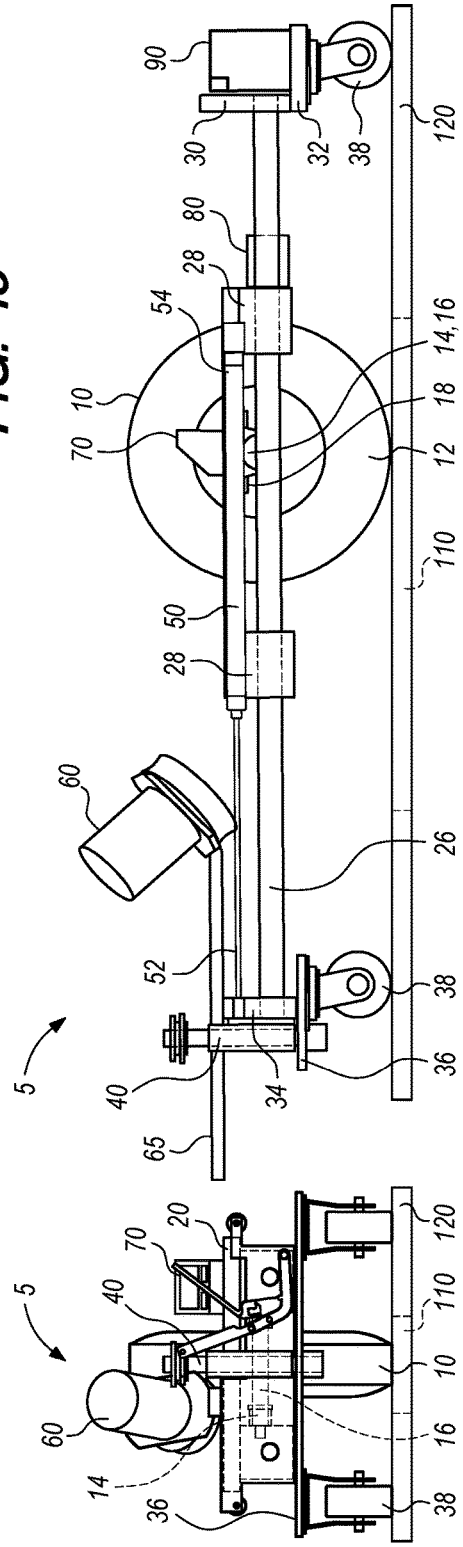
FIG. 19
FIG. 20
FIG. 21

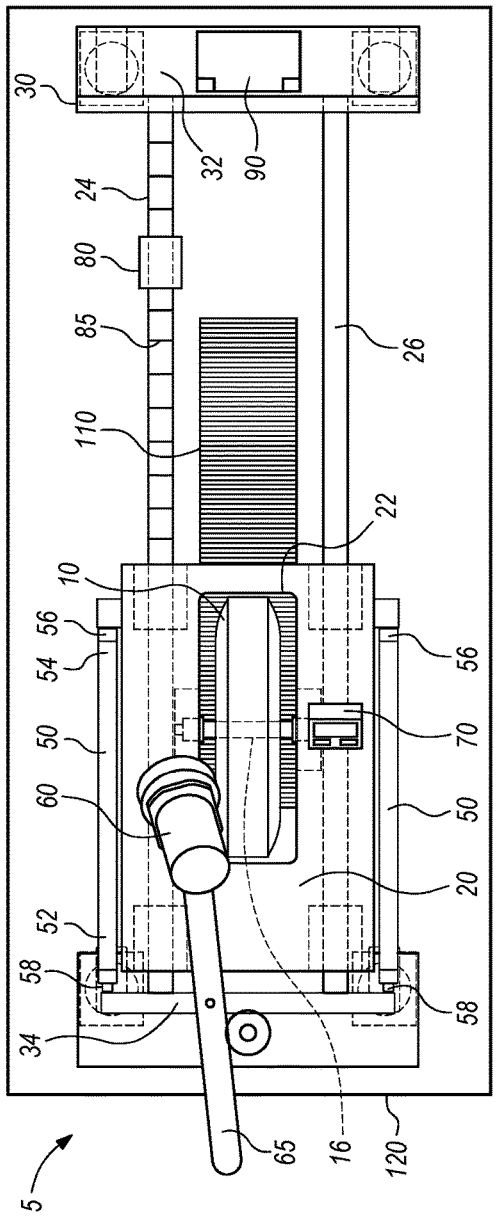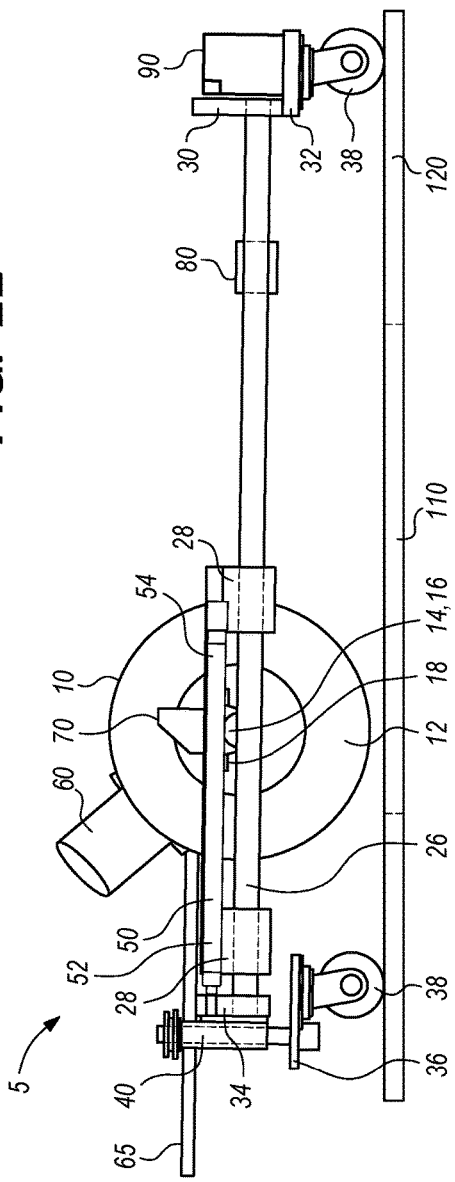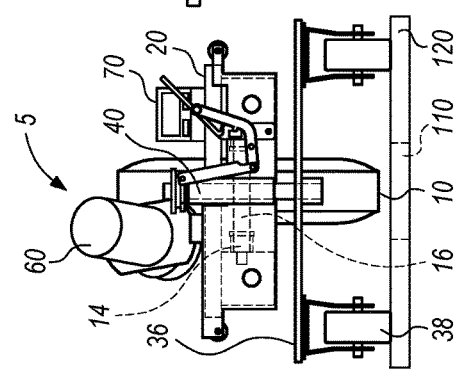
FIG. 22
FIG. 24
FIG. 23

PNEUMATIC RAM ROAD SURFACE COEFFICIENT OF FRICTION MEASURING DEVICE AND METHOD

BACKGROUND OF THE INVENTION

1. Field of the Invention

This invention relates to a roadway surface friction-measuring device and specifically to a stationary device that measures the coefficient of friction of a road surface using a known and precise amount of resistance force supplied from a pneumatic ram.

2. Description of Related Art

Friction is a measure of the amount of resistance force between two surfaces in contact with each other. Friction may also be described as the resistance that must be overcome if one mass is to slide across another. Friction is the force that allows all cars, trucks, and vehicles to travel on roads, streets, and highways. Friction between a vehicle's tires and the road surface causes the vehicle to move, accelerate, turn, stop, and so forth. Typically, the greater the friction between a vehicle's tires and the road surface, the easier it is for the vehicle to move, accelerate, turn, and stop. Driving safety typically increases with an increased amount of friction with the road.

The principally accepted scientific method for measuring friction between two surfaces is to measure the coefficient of friction between the surfaces. The coefficient of friction is a dimensionless scalar defined as: 'the force required to slide or move one object across a second object' divided by 'the normal force on the first object'. Since 1933, when Professor R. A. Moyer presented to the world a device to measure road surface friction, numerous other devices have been created to measure the coefficient of friction between a vehicle tire and a road surface. Most of these devices are designed to travel down the roadway while in operation, permanently attached to a vehicle/truck or towed behind a vehicle/truck. Most of these devices have a special 'testing tire' that comes in contact with the road surface to cause the testing tire to rotate as the vehicle or truck is traveling down the roadway. The testing tire has known and precise characteristics and the rotation of the testing tire is met with a known and precise amount of resistance force. The speed, rotations-per-minute, or other measurement of the rotating testing tire is determined as the device is traveling down the roadway, which is converted to a coefficient of friction measurement. An accurate conversion to coefficient of friction depends on calibration of the device against surfaces with very specifically known coefficients of friction.

Unlike those friction measuring devices, this invention is operational in a stationary condition. This invention may be moved to any specific location of a roadway for stationary placement and operation to measure the road surface coefficient of friction at that specific location. The portable aspect allows placement of the invention at a specific location on a roadway, such as the exact skid point of a vehicle that was involved in an accident or collision. Oftentimes, a measurement of friction at an exact point on a roadway is extremely helpful in resolving investigations and law suits regarding vehicle accidents or collisions.

All prior art road surface coefficient of friction measuring devices use a mechanical mechanism to supply the known and precise amount of resistance force to the testing tire or other mechanical appendage, where all of these mechanisms include one or more metal springs. Metal springs may be used to apply resistance directly to the testing tire or wheel, directly to the testing tire hub, indirectly to a brake pad or brake shoe attached to the testing tire hub, directly to a skid pad in contact with the road surface, directly to a skid pad in contact with the testing tire, or various other means. Applicant has used a road surface coefficient of friction measuring device with such a mechanical mechanism for many years. Applicant has discovered that metal springs on road surface coefficient of friction measuring devices can necessitate more frequent maintenance, replacement, and re-calibration than other components on the device. These issues are unavoidable with metal springs because metal springs must be made from relatively thin metal in order to be flexible; however, thin metal naturally fatigues or otherwise loses some of its shape or resilience over time, necessitating more frequent maintenance and calibration. The relatively short life cycle of metal springs on road surface coefficient of friction measuring devices can necessitate more frequent calibrations of the road surface coefficient of friction measuring device, where a lack of frequent calibrations can lead to inaccurate friction measurements. Accurate calibration is extremely important because it is required to receive an accurate coefficient of friction measurement from the device.

To solve these problems, Applicant has developed a pneumatic ram to apply a very precise and known amount of resistance force to a testing tire mounted on a portable and stationary friction measuring device, where the pneumatic ram is not subject to the frequent maintenance and replacement issues that face all other mechanical resistance mechanisms with one or more metal springs. Additionally, once the pneumatic ram is calibrated to the correct amount of resistance, it is not subject to the frequent recalibration requirements that face all other mechanical resistance mechanisms with one or more metal springs.

BRIEF SUMMARY OF THE INVENTION

It is an aspect of pneumatic ram road surface coefficient of friction measuring device to measure the coefficient of friction of a road surface.

It is an aspect of pneumatic ram road surface coefficient of friction measuring device to be a portable device that may be moved to any location of a roadway for the stationary placement and measuring of the coefficient of friction of the road surface.

It is an aspect of pneumatic ram road surface coefficient of friction measuring device to be calibrateable against a special surface such as a calibration plate with a known and precise coefficient of friction.

It is an aspect of pneumatic ram road surface coefficient of friction measuring device and method to comprise a special testing tire with known and precise characteristics mounted on a carriage plate that is slideably attached to a rail system that is pivotally attached to a framework that rests on the ground or roadway. One end of the rail system pivots upwards to raise the testing tire off of the road surface or calibration plate and pivots back downwards to lower the testing tire back down to contact the road surface or calibration plate. In the lowered position, the longitudinal axis of the rail system is parallel with that of the framework and the testing tire rests on the road surface or calibration plate. In the raised position, the longitudinal axis of the rail system forms an acute angle with that of the framework and the testing tire is lifted above the road surface or calibration plate and without contact therewith.

It is an aspect of pneumatic ram road surface coefficient of friction measuring device and method to comprise a means to lift or raise one end of the horizontal rail system upwards in order to raise the testing tire above the road surface or calibration plate, a means to hold the horizontal rail system in that raised position for a certain period of time, and a means to drop or release the raised end of horizontal rail system to allow gravity to cause it to fall back into the lower position to allow the testing tire to make contact with the road surface or calibration plate.

It is an aspect of pneumatic ram road surface coefficient of friction measuring device to comprise an motor that is used to drive the testing tire to a precise amount of rotations per minute while held above the road surface or calibration plate.

It is an aspect of pneumatic ram road surface coefficient of friction measuring device to cause the suspended rotating testing tire to drop or fall onto the road surface or calibration plate to undergo a controlled skid test across the road surface until it comes to rest.

It is an aspect of pneumatic ram road surface coefficient of friction measuring device to place a known and precise amount of resistance force on the testing tire as it undergoes the controlled skid test across the road surface or calibration plate.

It is an aspect of the known and precise amount of resistance force on the testing tire to be supplied by a non-mechanical means.

It is an aspect of the known and precise amount of resistance force on the testing tire to be supplied by one or more pneumatic rams.

It is an aspect of pneumatic ram road surface coefficient of friction measuring device to measure the distance traveled by the carriage plate after the rotating testing tire has completed a controlled skid test.

It is an aspect of pneumatic ram road surface coefficient of friction measuring device and method to determine the coefficient of friction between the testing tire and road surface based on the known characteristics of the testing tire rotating at a precise amount of rotations per minute and the distance traveled by the carriage plate.

It is an aspect of pneumatic ram road surface coefficient of friction measuring device and method to determine the coefficient of friction between the testing tire and road surface based on the precise and accurate calibration of the distance traveled by the carriage plate from a controlled skid test on a special calibration surface with a precisely known coefficient of friction.

It is an aspect of pneumatic ram road surface coefficient of friction measuring device and method to incorporate a special procedure to use this device to measure the coefficient of friction of a road surface including the steps of: placing the device at a specific location on a roadway; lifting the carriage plate to the raised position so that the testing tire is held above the road surface; holding the testing tire above the road surface; causing the rotation of the testing tire to a specific amount of rotations per minute; dropping the spinning testing tire onto the road surface to cause a controlled skid test of the testing tire; measuring the distance traveled by the testing tire from the controlled skid test to yield a coefficient of friction measurement between the testing tire and the road surface as indicated from a sliding gauge indicator.

It is an aspect of pneumatic ram road surface coefficient of friction measuring device and method to incorporate a special procedure to calibrate this device including the steps of: placing the device above a special calibration plate that is fixed or attached under the device; lifting the carriage plate to raised position so that the testing tire is held above the calibration plate; holding the testing tire above the calibration plate; causing the rotation of the testing tire to a specific amount of rotations per minute; dropping the spinning testing tire onto the calibration plate to cause a controlled skid test of the testing tire; measuring the distance traveled by the testing tire from the controlled skid test to yield a coefficient of friction measurement from a sliding gauge indicator; comparing the coefficient of friction measured by the sliding gauge indicator to the known amount for the calibration plate, slightly opening a calibration valve if the measurement is less than the known value or slightly closing a calibration valve if the measurement is greater than the known value, and repeating the above procedure until the coefficient of friction measured by the sliding gauge indicator matches the known amount.

BRIEF DESCRIPTION OF THE DRAWINGS

FIG. 1 is a top plan view of pneumatic ram road surface coefficient of friction measuring device with rotating testing tire held in the upper position, raised above the road surface, in preparation for the start of a measurement.

FIG. 2 is a front elevation view of pneumatic ram road surface coefficient of friction measuring device with rotating testing tire held in the upper position, raised above the road surface, in preparation for the start of a controlled skid test measurement.

FIG. 3 is a side elevation view of pneumatic ram road surface coefficient of friction measuring device with rotating testing tire held in the upper position, raised above the road surface, in preparation for the start of a measurement.

FIG. 4 is a top plan view of pneumatic ram road surface coefficient of friction measuring device with rotating testing tire in the lower position, in contact with the road surface at the beginning of a controlled skid test measurement.

FIG. 5 is a front elevation view of pneumatic ram road surface coefficient of friction measuring device with rotating testing tire in the lower position, in contact with the road surface at the beginning of a controlled skid test measurement.

FIG. 6 is a side elevation view of pneumatic ram road surface coefficient of friction measuring device with rotating testing tire in the lower position, in contact with the road surface at the beginning of a controlled skid test measurement.

FIG. 7 is a top plan view of pneumatic ram road surface coefficient of friction measuring device with still testing tire in the lower position, in contact with the road surface at the end of a controlled skid test measurement.

FIG. 8 is a front elevation view of pneumatic ram road surface coefficient of friction measuring device with still testing tire in the lower position, in contact with the road surface at the end of a controlled skid test measurement.

FIG. 9 is a side elevation view of pneumatic ram road surface coefficient of friction measuring device with still testing tire in the lower position, in contact with the road surface at the end of a controlled skid test measurement.

FIG. 10 is a top plan view of pneumatic ram road surface coefficient of friction measuring device with still testing tire held in the upper position and pulled back to the starting position after completing a controlled skid test while leaving the sliding gauge indicator in the position marking the length traveled by carriage plate from the controlled skid test.

FIG. 11 is a front elevation view of pneumatic ram road surface coefficient of friction measuring testing with still testing tire held in the upper position and pulled back to the starting position after completing a controlled skid test while leaving the sliding gauge indicator in the position marking the length traveled by carriage plate from the controlled skid test.

FIG. 12 is a side elevation view of pneumatic ram road surface coefficient of friction measuring device with still testing tire held in the upper position and pulled back to the starting position after completing a controlled skid test while leaving the sliding gauge indicator in the position marking the length traveled by carriage plate from the controlled skid test.

FIG. 13 is a top plan view of pneumatic ram road surface coefficient of friction measuring device with rotating testing tire held in the upper position, raised above a calibration plate secured by a calibration plate holder in preparation for the start of a calibration test.

FIG. 14 is a front elevation view of pneumatic ram road surface coefficient of friction measuring device with rotating testing tire held in the upper position, raised above a calibration plate secured by a calibration plate holder in preparation for the start of a calibration test.

FIG. 15 is a side elevation view of pneumatic ram road surface coefficient of friction measuring device with rotating testing tire held in the upper position, raised above a calibration plate secured by a calibration plate holder in preparation for the start of a calibration test.

FIG. 16 is a top plan view of pneumatic ram road surface coefficient of friction measuring device with rotating testing tire in the lower position, in contact with a calibration plate at the beginning of a controlled skid test calibration test.

FIG. 17 is a front elevation view of pneumatic ram road surface coefficient of friction measuring device with rotating testing tire in the lower position, in contact with a calibration plate at the beginning of a controlled skid test calibration test.

FIG. 18 is a side elevation view of pneumatic ram road surface coefficient of friction measuring device with rotating testing tire in the lower position, in contact with a calibration plate at the beginning of a controlled skid test calibration test.

FIG. 19 is a top plan view of pneumatic ram road surface coefficient of friction measuring device with still testing tire in the lower position, in contact with a calibration plate at the end of a controlled skid test calibration test.

FIG. 20 is a front elevation view of pneumatic ram road surface coefficient of friction measuring device with still testing tire in the lower position, in contact with a calibration plate at the end of a controlled skid test calibration test.

FIG. 21 is a side elevation view of pneumatic ram road surface coefficient of friction measuring device with still testing tire in the lower position, in contact with a calibration plate at the end of a controlled skid test calibration test.

FIG. 22 is a top plan view of pneumatic ram road surface coefficient of friction measuring device with still testing tire in the upper position and pulled back to the starting position after completing a controlled skid test calibration test while leaving the sliding gauge indicator in the position marking the length traveled by carriage plate from the controlled skid test calibration test.

FIG. 23 is a front elevation view of pneumatic ram road surface coefficient of friction measuring with still testing tire in the upper position and pulled back to the starting position after completing a controlled skid test calibration test while leaving the sliding gauge indicator in the position marking the length traveled by carriage plate from the controlled skid test calibration test.

FIG. 24 is a side elevation view of pneumatic ram road surface coefficient of friction measuring device with still testing tire in the upper position and pulled back to the starting position after completing a controlled skid test calibration test while leaving the sliding gauge indicator in the position marking the length traveled by carriage plate from the controlled skid test calibration test.

DEFINITION LIST

Figure 25:
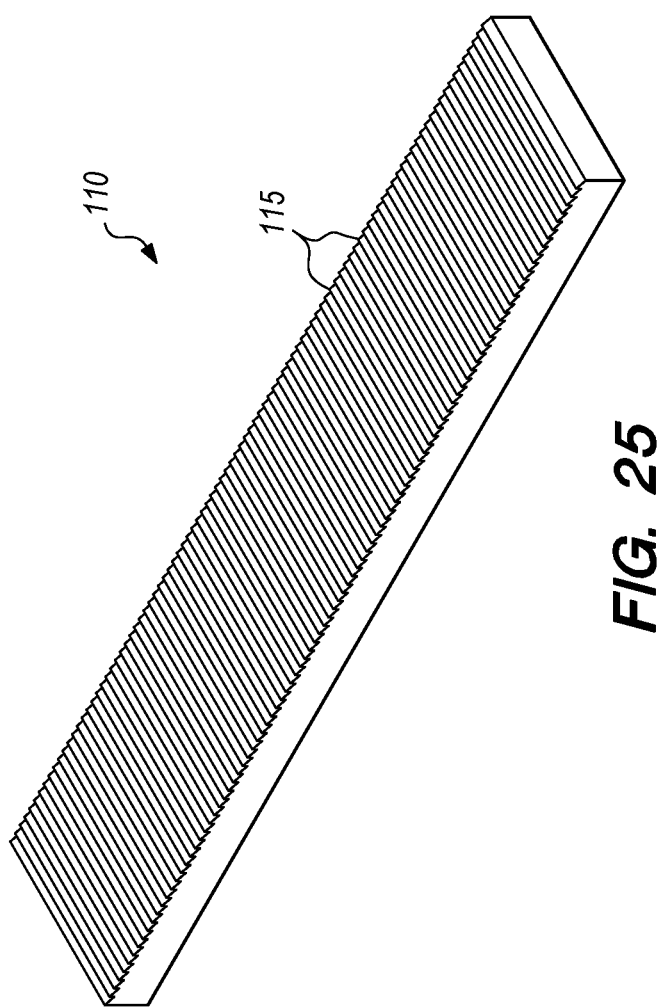
FIG. 25 is a top perspective view of a calibration plate depicting parallel ridges on the top surface thereof.

| Term | Definition |
| --- | --- |
| 5 | Pneumatic Ram Road Surface Coefficient of Friction Measuring Device |
| 10 | Testing Tire |
| 12 | Wheel |
| 14 | Bearing |
| 16 | Axle |
| 18 | Axle Mounting Bracket |
| 20 | Carriage Plate |
| 22 | Tire Clearance Hole |
| 24 | Left Rail |
| 26 | Right Rail |
| 28 | Rail Mount |
| 30 | Front Rail Plate |
| 32 | Front Caster Plate |
| 34 | Rear Rail Plate |
| 36 | Rear Caster Plate |
| 38 | Caster |
| 40 | Jack Mechanism |
| 50 | Pneumatic Ram |
| 52 | Piston Side |
| 54 | Cylinder Side |
| 56 | Air Vent |
| 58 | Calibration Valve |
| 60 | Motor |
| 65 | Motor Mounting Arm |
| 70 | Tachometer |
| 80 | Sliding Gauge Indicator |
| 85 | Coefficient of Friction Graduations |
| 90 | Battery |
| 100 | Road Surface |
| 110 | Calibration Plate |
| 115 | Parallel Ridges |
| 120 | Calibration Plate Holder |

DETAILED DESCRIPTION OF THE INVENTION

Pneumatic ram road surface coefficient of friction measuring device 5 comprises: a testing tire 10 mounted on a wheel 12 that is rigidly attached to an axle 16, which is pivotally attached a carriage plate 20 by two bearings 14. Testing tire 10 is a special tire with known and predictable characteristics and properties. Testing tire 10 is a specific tire with specific size, air pressure, elastomer material, ply construction, tread quality, tread surface, and ASTM number. Pivotal attachment is such that testing tire 10 and wheel 12 may freely rotate around axle 16 without any appreciable resistance or friction.

Pneumatic ram road surface coefficient of friction measuring device 5 further comprises a carriage plate 20. Carriage plate 20 is a rigid rectangular cuboid member with a top surface, a bottom surface, a left surface, a right surface, a front surface, and a rear surface. Carriage plate 20 is about 1-4 feet wide, 2-8 feet long, and 0.125 to 4 inches thick.

Axle 16 is pivotally attached to carriage plate 20 by two bearings 14, one at each end of axle 16. Each bearing 14 is rigidly attached to carriage plate 20 by an axle mounting bracket 18. Bearings 14 may be any known type of bearing to secure axle 16 to carriage plate 20 by axle mounting bracket 18, while still allowing axle 16 to freely rotate along its longitudinal axis. The longitudinal axis of axle 16 is parallel with the front and rear surfaces of carriage plate 20 and with the plane of the carriage plate 20. Carriage plate 20 further comprises a tire clearance hole 22. Tire clearance hole 22 is a rectangular shaped void in carriage plate 20 with its longitudinal axis parallel with that of carriage plate 20. Testing tire 10 and wheel 12 are mounted within tire clearance hole 22 so that about half of the tire and wheel 10,12 extends above the top surface of carriage plate 20 and about half of the tire and wheel 10,12 extends below the bottom surface of carriage plate 20 as depicted. Tire clearance hole 22 must be larger than the top plan view rectangular footprint of testing tire 10 in order to provide enough clearance for the testing tire 10 to be mounted therein. Axle mounting brackets 18 may be mounted to the top surface or bottom surface of carriage plate 20.

Pneumatic ram road surface coefficient of friction measuring device 5 further comprises a left rail 24 and a right rail 26. Left rail 24 and right rail 26 are each a rail or rigid oblong member with a front end and a rear end. Left and right rails 24,26 are about 1-8 feet longer than the length of carriage plate 20. Left and right rails 24,26 are positioned parallel with each other and with their ends in even alignment as depicted. Left rail 24 is positioned adjacent and parallel to the left surface of carriage plate 20. Left rail 24 may be positioned underneath, along side of, or above the left surface of carriage plate 20. Right rail 26 is positioned adjacent and parallel to the right surface of carriage plate 20. Right rail 26 is positioned underneath, along side of, or above the right surface of carriage plate 20. The front ends of rails 24,26 are each rigidly attached to the rear surface of a front rail plate 30. Front rail plate 30 is a rigid rectangular cuboid member with a front, rear, top, bottom, left, and right surface. The bottom surface of front rail plate 30 is rigidly attached to the top surface of a front caster plate 32. Front caster plate 32 is a rigid horizontal rectangular cuboid member with a front, rear, top, bottom, left, and right surface. One of more casters 38 may be attached to the bottom surface of front caster plate 32. In best mode, two casters 38 are attached to the bottom surface of front caster plate 32, as depicted. The rear ends of rails 24,26 are each rigidly attached to the front surface of a rear rail plate 34. Rear rail plate 34 is a rigid rectangular cuboid member with a front, rear, top, bottom, left, and right surface. The bottom surface or rear surface of rear rail plate 34 is rigidly attached to a top end of a jack mechanism 40. A bottom end of the jack mechanism 40 is rigidly attached to the top surface of a rear caster plate 36. Rear caster plate 36 is a rigid horizontal rectangular cuboid member with a front, rear, top, bottom, left, and right surface. One of more casters 38 may be attached to the bottom surface of rear caster plate 36. In best mode, two casters 38 are attached to the bottom surface of rear caster plate 36, as depicted. The bottom surfaces of front and rear caster plates 32,36 rest on the road surface 100 or on a calibration plate holder 120. If casters 38 are used, casters 38 rest on the road surface 100 or on a calibration plate holder 120, as depicted.

Testing tire 10 and wheel 12 are located between left rail 24 and right rail 26 as depicted. Carriage plate 20 is slideably attached to left rail 24 adjacent to its left surface and slideably attached to right rail 26 adjacent to its right surface. Rails 24,26 provide smooth linear slideable movement of carriage plate 20 along the length of rails 24,26. Linear slideable attachment is accomplished with four rail mounts 28. Each rail mount 28 is rigidly attached to the bottom surface of carriage plate 20 and slideably attached to left rail 24 or right rail 26. Rail mounts 28 rigidly attach to carriage plate 20 but may slide along the full length of rails 24,26 without becoming disconnected therefrom. This slideable connection allows the carriage plate 20 to slide back and forth along the length of rails 24,26 without becoming disconnected therefrom. Rail mounts 28 and carriage plate 20 slide along rails 24,26 with little to no resistance force. Any known type of rail may be used for left rail 24 or right rail 26. Any known type of mounting structure, connector, rail shoe, or wheel may be used for rail mounts 28 to slideably attach to rails 24,26. The slideable attachment of the carriage plate to rails 24,26 has minimal friction and allows for linear motion of the carriage plate along the rail system with small resistance force. The rearward most position is the start position for carriage plate 20 for a controlled skid test. Carriage plate 20 moves forward during a controlled skid test and rests in a forward position after a controlled skid test is completed.

The whole assembly of testing tire 10, carriage plate 20, rails 24,26, and rail plates 30,34 may be rotated about the front end of pneumatic ram road surface coefficient of friction measuring device 5 to be held in an upper position or dropped to a lower position. In the upper position, rear rail plate 34 is lifted and rotated upwards and held there so that carriage plate 20 and rails 24,26 form an acute angle with the road surface 100 or calibration plate 110 and testing tire 10 is not in contact with the road surface 100 or calibration plate 110, as depicted in FIGS. 1-3, 10-15, and 22-24. In the upper position, jack mechanism 40 supports the rear rail plate 34 above rear caster plate 36 to create a gap of about 1-10 inches there between. The gap between rear rail plate 34 and rear caster plate 36 is approximately equal to gap between testing tire 10 and road surface 100 when pneumatic ram road surface coefficient of friction measuring device 5 is in the upper position. As described below, jack mechanism 40 is used to lift, hold, and release rear rail plate 34 from the upper position to the lower position. In the lower position, carriage plate 20 and rails 24,26 are parallel with the road surface 100 or calibration plate 110 and testing tire 10 is in contact with the road surface 100 or calibration plate 110, as depicted in FIGS. 4-9 and 16-21. In the lower position, the bottom surface of rear rail plate 34 rests on the top surface of rear caster plate 36. Pneumatic ram road surface coefficient of friction measuring device 5 is designed so that, in the lower position, there exists a certain, precise, and accurate amount of downward force on testing tire 10 as required to yield accurate friction measurements. As described below, jack mechanism 40 is used to raise pneumatic ram road surface coefficient of friction measuring device 5 into the upper position. As described below, jack mechanism 40 is used to drop pneumatic ram road surface coefficient of friction measuring device 5 into the lower position.

Pneumatic ram road surface coefficient of friction measuring device 5 further comprises at least one pneumatic ram 50. Resistance force is applied to the sliding motion of the carriage plate 20 by at least one pneumatic ram 50. At least one pneumatic ram 50 comprises a rod member attached to a piston member slideably attached to the inside of a cylinder member. Rod member is a rigid oblong member with a front end and a rear end. Piston member is a rigid solid cylindrical shaped member with a front end, a rear end, and an outside diameter that is sized to make an airtight slip fit with the inside diameter of cylinder member. Cylinder member is a rigid hollow cylindrical shaped member with a front end, a rear end, and an inside diameter. The front end of piston member slides into the rear end cylinder member to slideably attach within the interior of cylinder member. The front end of a rod member is attached to the rear end of piston member. The rear end of rod member extends out from the rear end of cylinder member and rigidly attaches to the front surface of rear rail plate 34. The front end of cylinder member is rigidly attached to carriage plate 20 or to a rail mount 28. With this design, any motion of carriage plate 20 along rails 24,26 causes an equivalent length of motion of the piston member inside the cylinder member of pneumatic ram 50.

At least one pneumatic ram 50 comprises an air vent 56 and a calibration valve 58. The front end of cylinder member has an airtight closed end with an air vent 56 located therein. The rear end of cylinder member has an airtight closed end with a calibration valve 58 located therein. Because of the airtight slip fit between the outside diameter of piston member and the inside diameter of cylinder member, air must be added to the space between the front end of cylinder member and the front end of piston member and concurrently subtracted from the space between the rear end of cylinder member and the rear end of piston member, as carriage plate 20 is moved rearward. Correspondingly, because of the airtight slip fit between the outside diameter of piston member and the inside diameter of cylinder member, air must be subtracted from the space between the front end of cylinder member and the front end of piston member and concurrently added to the space between the rear end of cylinder member and the rear end of piston member, as carriage plate 20 is moved forward. During a controlled skid test across a road surface 100 or across a calibration plate 110, carriage plate 20 starts from rest, at point adjacent to rear rail plate 34, then slides forward, towards the front rail plate 30, to come to rest again prior to contacting or touching the front rail plate 34.

This invention uses pneumatic principles to create an accurate and precise resistance force on the travel of carriage plate 20 while on a controlled skid test across a test surface. Air vent 56 is a small orifice in the front end of cylinder member with diameter of about 0.001 to 0.100 of an inch. Air vent 56 functions to allow air to vent into the cylinder member as the carriage plate 20 is moved rearwards, and to vent air out of the cylinder member as the carriage plate 20 is moved forwards. Calibration Valve 58 is an air valve on the rear end of cylinder member. Calibration valve 58 functions to allow air to vent into the cylinder member as the carriage plate 20 is moved forwards, and to vent air out of the cylinder member as the carriage plate 20 is moved rearwards. Calibration valve 58 is an adjustable air valve that may be adjusted to a fully closed airtight position or to a fully open position to allow air to freely flow according to pressure variations. Calibration valve 58 may be any known type of adjustable air valve. The orifice diameter of air vent 56 should be larger than that of calibration valve 58 when calibrated.

Calibration valve 58 must be calibrated in order for pneumatic ram road surface coefficient of friction measuring device 5 to measure friction accurately. Calibration is the process of adjusting and locking calibration valve 58 in a very exact and specific position that is partially open and partially closed, that allows for the exact correct amount of airflow through calibration valve 58, to enter the space between the rear end of piston member and the rear end of cylinder member, as carriage plate 20 is moving forward during a controlled skid test. The resistance force applied to carriage plate 20 during a controlled skid test is directly proportional to the adjustment or setting position on calibration valve 58.

Once calibration valve 58 is calibrated, the precise and accurate amount of resistance force stays constant over extended periods of time, such as many years. On the other hand, the resistance force applied by a mechanical spring does not remain constant over a period of many years because the metal in the spring fatigues, as stated above. Pneumatic ram road surface coefficient of friction measuring device 5 has an advantage in this regard because the resistance force applied by pneumatic ram 50 is highly repeatable and requires very infrequent recalibration to remain precise. Additionally, the pneumatic ram 50 has a substantially longer life and maintenance cycle than those of metal springs.

Best mode pneumatic ram road surface coefficient of friction measuring device 5 comprises two pneumatic rams 50. With two pneumatic rams 50, one may be placed on each side of carriage plate 20 to allow the application of more even resistance force to carriage plate 20 as it completes a controlled skid test than would be the case if only one pneumatic ram 50 were used. Only one calibration valve 58 is connected to both pneumatic rams 50 in order to provide one calibration control point to calibrate both pneumatic rams 50 and to yield even resistance force from each pneumatic ram 50. With this design, the one calibration valve 58 is connected via tubing or piping to the rear end of each cylinder member of each pneumatic ram 50 so that the calibration valve 58 has an airtight connection with or pneumatically coupled to the rear end of each cylinder member via the tubing or piping.

Pneumatic ram road surface coefficient of friction measuring device 5 further comprises a jack mechanism 40. Jack mechanism 40 is a means to lift and hold rear rail plate 34 in an upper position further above rear caster plate 36, so that testing tire 10 is raised above road surface 100 or calibration plate 110 and not in contact therewith. Jack mechanism 40 holds testing tire 10 above and out of contact with the road surface 100 or calibration plate 110 so that testing tire 10 may be rotated and brought up to the proper rotational speed in order to conduct a proper skid test and friction measurement, which could not be done if testing tire 10 were in contact with the road surface 100 or calibration plate 110. Jack mechanism 40 is also a means to drop or release rear rail plate 34 so that it falls back down towards the rear caster plate 36 from the upper position, to allow the rotating testing tire 10 to regain contact with road surface 100 or calibration plate 110 in order to start a controlled skid test. Thus, jack mechanism 40 is a means to: lift rear rail plate 34 from a lower horizontal position to an upper position, hold rear rail plate 34 in the upper position, and release rear rail plate 34 from the upper position to let it fall back down to the lower position. Jack mechanism 40 has a bottom end and a top end. The bottom end of jack mechanism 40 is attached to or supported by the upper surface of rear caster plate 36. The top end of jack mechanism 40 is attached to the lower surface of rear rail plate 34. Any known means to lift, hold, and release may be used, such as: a screw jack, a hydraulic jack, a pneumatic jack, one or more solenoid valves, a lever and fulcrum, a line and pulley, or other. Best mode is a special lever and fulcrum mechanism that raises rear rail plate 34 with a one-half rotation of the lever about the fulcrum, and then releases or drops the rear rail plate 34 with the sliding of the lever off of the fulcrum. The purpose of lifting rear rail plate 34 is to lift testing tire 10 upwards and out of contact with the road surface 100 or calibration plate 110. jack mechanism 40 should lift testing tire 10 about 0.25-5 inches above the road surface 100 or calibration plate 110. Testing tire 10 must be raised so that it can be driven by a motor 60 to attain the precise amount of rotations per minute before being dropped onto the road surface 100 or calibration plate 110 to undergo a controlled skid test. The length traveled by testing tire 10 as a result of the controlled skid test is proportional to the coefficient of friction of the testing surface. The length traveled by the testing tire 10 as a result of the controlled skid test is typically about 0.5 to 3 feet.

Pneumatic ram road surface coefficient of friction measuring device 5 further comprises: a sliding gauge indicator 80 and a set of coefficient of friction graduations 85. Sliding gauge indicator 80 and set of coefficient of friction graduations 85 function to measure the precise distance traveled by testing tire 10 as a result of a controlled skid test. Sliding gauge indicator 80 is a rigid member with a front edge and a rear edge that is slideably attached to left rail 24 or right rail 26, positioned just in front of carriage plate 20. Sliding gauge indicator 80 has a geometrical shape designed to slideably attach onto rail 24 or 26 so that sliding gauge indicator 80 is prevented from detaching or breaking away therefrom but may be freely moved or slid along the longitudinal axis of rail 24 or 26. Any known slideable attachment means or connection type may be used. In best mode, rails 24,26 are cylindrical-shaped and sliding gauge indicator 80 is also cylindrical shaped with an inner diameter sized to make a slip fit with the outer diameter of rails 24 and 26. Coefficient of friction graduations 85 are markings on the left rail 24 or right rail 26, or, alternately on a scale, a tape, or a ruler attached to the left rail 24 or to the right rail 26. Coefficient of friction graduations 85 represent a coefficient of friction scale from about 0.1 to 0.5. Before a controlled skid test is conducted, sliding gauge indicator 80 is slid all the way back towards the rear rail plate 34, which is the zero position of the scale. Then the controlled skid test is conducted to cause forward movement of carriage plate 20, which causes forward movement of sliding gauge indicator 80. After the controlled skid test is completed, the sliding gauge indicator 80 marks the distance traveled by the carriage plate 20. The scale of coefficient of friction graduations 85 is not in a distance scale, but rather in a dimensionless 'coefficient of friction' scale. Road surfaces with greater the coefficients of friction yield longer controlled skid tests. Thus, larger coefficient of friction graduations are located towards the front of the device and the zero marking is located at the rear of the device. Applicant has determined the exact placement and scale of coefficient of friction graduations 85 from many years of research, development, and actual use skid test devices using the specified testing tire on calibrations plates with exactly known and precise coefficients of friction, where the precise known values have been repeatedly verified by other friction testing devices.

Pneumatic ram road surface coefficient of friction measuring device 5 further comprises a motor 60 and a motor mounting arm 65. Motor 60 is used to cause the rotation of testing tire 10 prior to the dropping of rotating testing tire 10 onto the road surface 100 or calibration plate 110 to start a controlled skid test. Motor 60 may be any known type of motor with a drive shaft. In best mode, motor 60 is an electric motor. In this case, Pneumatic ram road surface coefficient of friction measuring device 5 further comprises a battery 90 that has electrical continuity with motor 60. Battery 90 is a direct current electrical power source. Motor mounting arm 65 is a rigid oblong horizontal member with a front end, a mid-section, and a rear end. Motor 60 is rigidly attached or mounted to the front end of motor mounting arm 65. The mid-section of motor mounting arm 65 is pivotally attached to the top surface, front surface, or rear surface of rear rail plate 34. Pivotal attachment is such that the rear end of motor mounting arm 65 may be adjusted or manipulated horizontally to swing the front end of motor mounting arm 65 horizontally away from or towards the side of testing tire 10 as depicted. In this way, the motor 60 attached to the front end of motor mounting arm 65 may be horizontally swung or rotated so that its driveshaft comes in contact with the side of testing tire 10 when carriage plate 20 is in its rearward starting position and may also be horizontally swung or rotated out of contact with the side of testing tire 10 when carriage plate 20 is in its rearward starting position. In best mode there is a springed or tensioned bias on the pivotal attached to pull or retract motor 60 away from testing tire 10.

Pneumatic ram road surface coefficient of friction measuring device 5 further comprises a tachometer 70 attached to wheel 12 or axle 16. Tachometer 70 is an RPM gauge used to measure the rotations per minute of testing tire 10. Tachometer 70 may have electrical continuity with battery 90 or may have its own internal power source.

Pneumatic ram road surface coefficient of friction measuring device 5 is calibrated with the use of a calibration plate 110. Calibration plate 110 is a rigid rectangular planar member with a top surface, a bottom surface, a left edge, a right edge, a front edge, and a rear edge. The left and right edges are the long sides of rectangular planar member and the front and rear edges are the short sides of rectangular planar member. The top surface of calibration plate 110 has a plurality of parallel ridges 115 running from the left edge to the right edge, across the entire top surface. Parallel ridges 115 are vertical ridges that are parallel with each other and parallel with the front and rear edges of calibration plate 110. Each parallel ridge 115 has a height of about 0.005 to 0.100 inches and a spatial frequency of about 0.010 to 0.250 inches. Parallel ridges 115 have very precise geometry that has a specific and known coefficient of friction. Applicant has many years of experience with the design and development of calibration plates 110 with parallel ridges 115. Applicant has a plurality of calibration plates 110 with precise and accurately formed parallel ridges 115 on the top surface thereof where a precise and accurate coefficient of friction is known and verified for the top surface of each. One method used by Applicant to determine and verify the precise and accurate coefficient of friction of each calibration plate 110 is through the use of elaborate measuring equipment developed by Professor R. A. Moyer.

During the calibration procedure, calibration plate 110 is held into place with a calibration plate holder 120. Calibration plate holder 120 is a rigid rectangular horizontal planar member with a top surface, a bottom surface, a left edge, a right edge, front edge, and a rear edge. Calibration plate holder 120 is slightly longer than pneumatic ram road surface coefficient of friction measuring device 5 as depicted. Calibration plate holder 120 is slightly wider than pneumatic ram road surface coefficient of friction measuring device 5 as depicted. Calibration plate holder 120 has a mounting hole, wherein calibration plate 110 is mounted, as depicted. Mounting hole is a rectangular shaped void in calibration plate holder 120 with its longitudinal axis parallel with that of calibration plate holder 120. Mounting hole has a length and width that is slightly larger than those of calibration plate 110 so that calibration plate 110 has a slip fit within mounting hole. When calibration plate 110 is placed within mounting hole, calibration plate 110 is held still and free from movement or vibration relative to calibration plate holder 120. In order to run the calibration procedure, calibration plate 110 and calibration plate holder 120 must be positioned underneath pneumatic ram road surface coefficient of friction measuring device 5, as depicted.

In best mode, pneumatic ram road surface coefficient of friction measuring device 5 is a towable trailer in and of itself. In best mode, pneumatic ram road surface coefficient of friction measuring device 5 may be towed by any vehicle with a trailer hitch, such as a pickup truck or van with a trailer hitch. In best mode, pneumatic ram road surface coefficient of friction measuring device 5 further comprises a trailer coupler (not depicted) rigidly attached to the front surface or top surface of front caster plate 32 or to the front surface or top surface of front rail plate 30. Alternately, trailer coupler may be attached indirectly to front caster plate 32 or to front rail plate 30 through a rigid structural assembly or lattice structure. Trailer coupler may be any known attachment means or connector used to reversibly attach to a trailer hitch on a vehicle. Best mode trailer coupler is a coupler designed to fit a trailer hitch with a hitch ball. With this design, pneumatic ram road surface coefficient of friction measuring device 5 may be easily transported to any desired location on a road surface by towing.

This design has the additional benefit of securing the pneumatic ram road surface coefficient of friction measuring device 5 during a skid test. Pneumatic ram road surface coefficient of friction measuring device 5 is held stationary when the tow vehicle is parked. The tow vehicle acts as an anchor to hold pneumatic ram road surface coefficient of friction measuring device 5 still during skid testing. Pneumatic ram road surface coefficient of friction measuring device 5 must be kept still during a skid test to insure that all movement on the sliding gauge indicator 80 resulted from the testing tire 10 moving skidding across the road surface 100 and not from any movement of the whole pneumatic ram road surface coefficient of friction measuring device 5 over the road surface 100 because this would yield an inaccurate measurement of friction of road surface 100.

The procedure to calibrate pneumatic ram road surface coefficient of friction measuring device 5 comprises the following steps.

a. Position calibration plate holder 120 on a level surface and secure thereto.
b. Mount calibration plate 110 into mounting hole on calibration plate holder 120.
c. Engage jack mechanism 40 to place pneumatic ram road surface coefficient of friction measuring device 5 into the upper position.
d. Pull the carriage plate 20 to its rear most position, with its rear surface resting against the front surface of rear rail plate 34.
e. Position pneumatic ram road surface coefficient of friction measuring device 5 entirely on top of calibration plate holder 120 with the longitudinal axis of pneumatic ram road surface coefficient of friction measuring device 5 is parallel with that of calibration plate holder 120 and testing tire 10 is positioned directly above calibration plate 110, adjacent to its rear edge as depicted in FIGS. 13-15.
f. Set sliding gage indicator 80 to the zero position that is the rear most position, with its rear edge resting against the front surface of front rail plate 30.
g. Rotate motor mounting arm 65 so that motor 60 comes into contact with testing tire 10.
h. Start motor 60 to cause the rotation of motor 60 and testing tire 10.
i. Stop motor 60 when the rotation of testing tire 10 reaches a first designated rotations per minute rate, which is greater than a second designated rotations per minute rate.
j. Rotate motor mounting arm 65 so that motor 60 comes out of contact with testing tire 10.
k. Allow the test tire 10 to decrease its rotations per minute rate due to friction to the second designated rotations per minute rate. (In best mode, second designated rotations per minute rate is 1050 RPM.)
l. Release jack mechanism 40 to drop pneumatic ram road surface coefficient of friction measuring device 5 to the lower position, thereby dropping the rotating testing tire 10 onto the upper surface of calibration plate 110 with testing tire 10 rotating at the second designated rotations per minute rate.
m. Allow testing tire 10 to skid along the upper surface of calibration plate 110 until testing tire 10 comes to rest, thereby completing a controlled skid test.
n. Note the coefficient of friction indicated by the sliding gauge indicator 80 on coefficient of friction graduations 85.
o. Compare the noted coefficient of friction with the known coefficient of calibration plate 110.
p. If these are not equivalent, adjust calibration valve 58 to adjust carriage plate 20 travel distance or coefficient of friction reading as necessary.
q. If noted coefficient of friction is greater than the known coefficient of friction, increase resistance induced by pneumatic ram 50 by partially closing calibration valve 58 in order to decrease carriage plate 20 travel distance or coefficient of friction reading.
r. If noted coefficient of friction is less than the known coefficient of friction, decrease resistance induced by pneumatic ram 50 by partially opening calibration valve 58 to increase carriage plate 20 travel distance or coefficient of friction reading.
s. Repeat the preceding steps as necessary until the sliding gauge indicator 80 matches the known coefficient of friction of calibration plate 110 on coefficient of friction graduations 85 within about 0.02.

Alternately, the procedure to calibrate pneumatic ram road surface coefficient of friction measuring device 5 comprises the following steps.

a. Position calibration plate holder 120 on a level surface and secure thereto.
b. Mount calibration plate 110 into mounting hole on calibration plate holder 120.
c. Engage jack mechanism 40 to place pneumatic ram road surface coefficient of friction measuring device 5 into the upper position.
d. Pull the carriage plate 20 to its rear most position, with its rear surface resting against the front surface of rear rail plate 34.
e. Position pneumatic ram road surface coefficient of friction measuring device 5 entirely on top of calibration plate holder 120 with the longitudinal axis of pneumatic ram road surface coefficient of friction measuring device 5 is parallel with that of calibration plate holder 120 and testing tire 10 is positioned directly above calibration plate 110, adjacent to its rear edge as depicted in FIGS. 13-15.
f. Set sliding gage indicator 80 to the zero position that is the rear most position, with its rear edge resting against the front surface of front rail plate 30.
g. Cover or wet the full circumference of the testing tire 10 with glycerin.

h. Cover or wet the entire upper surface of calibration plate 110 with glycerin.
i. Rotate motor mounting arm 65 so that motor 60 comes into contact with testing tire 10.
j. Start motor 60 to cause the rotation of motor 60 and testing tire 10.
k. Stop motor 60 when the rotation of testing tire 10 reaches a first designated rotations per minute rate, which is greater than a second designated rotations per minute rate.
l. Rotate motor mounting arm 65 so that motor 60 comes out of contact with testing tire 10.
m. Allow the test tire 10 to decrease its rotations per minute rate due to friction to the second designated rotations per minute rate. (In best mode, second designated rotations per minute rate is 1050 RPM.)
n. Release jack mechanism 40 to drop pneumatic ram road surface coefficient of friction measuring device 5 to the lower position, thereby dropping the rotating testing tire 10 onto the upper surface of calibration plate 110 with testing tire 10 rotating at the second designated rotations per minute rate.
o. Allow testing tire 10 to skid along the upper surface of calibration plate 110 until testing tire 10 comes to rest, thereby completing a controlled skid test.
p. Note the coefficient of friction indicated by the sliding gauge indicator 80 on coefficient of friction graduations 85.
q. Compare the noted coefficient of friction with the known coefficient of calibration plate 110.
r. If these are not equivalent, adjust calibration valve 58 to adjust carriage plate 20 travel distance or coefficient of friction reading as necessary.
s. If noted coefficient of friction is greater than the known coefficient of friction, increase resistance induced by pneumatic ram 50 by partially closing calibration valve 58 in order to decrease carriage plate 20 travel distance or coefficient of friction reading.
t. If noted coefficient of friction is less than the known coefficient of friction, decrease resistance induced by pneumatic ram 50 by partially opening calibration valve 58 to increase carriage plate 20 travel distance or coefficient of friction reading.
u. Repeat the preceding steps as necessary until the sliding gauge indicator 80 matches the known coefficient of friction of calibration plate 110 on coefficient of friction graduations 85 within about 0.02.

The procedure to use pneumatic ram road surface coefficient of friction measuring device 5 in order to measure the coefficient of friction of a road surface 100 comprises the following steps.
a. Position pneumatic ram road surface coefficient of friction measuring device 5 on a road surface 100 so that testing tire 10 is positioned above the position on the road surface 100 that requires measuring.
b. Secure pneumatic ram road surface coefficient of friction measuring device 5 from any movement relative to road surface 100.
c. Engage jack mechanism 40 to place pneumatic ram road surface coefficient of friction measuring device 5 into the upper position.
d. Pull the carriage plate 20 to its rear most position, with its rear surface resting against the front surface of rear rail plate 34.
e. Set sliding gage indicator 80 to the zero position that is the rear most position, with its rear edge resting against the front surface of front rail plate 30.
f. Rotate motor mounting arm 65 so that motor 60 comes into contact with testing tire 10.
g. Start motor 60 to cause the rotation of testing tire 10.
h. Stop motor 60 when the rotation of testing tire 10 reaches a first designated rotations per minute rate, which is greater than a second designated rotations per minute rate.
i. Rotate motor mounting arm 65 so that motor 60 comes out of contact with testing tire 10.
j. Allow the test tire 10 to decrease its rotations per minute rate due to friction to the second designated rotations per minute rate. (In best mode, second designated rotations per minute rate is 1050 RPM.)
k. Release jack mechanism 40 to drop pneumatic ram road surface coefficient of friction measuring device 5 to the lower position, thereby dropping the rotating testing tire 10 onto to road surface 100 with testing tire 10 rotating at the second designated rotations per minute rate.
l. Allow testing tire 10 to skid along the road surface 100 until testing tire 10 comes to rest, thereby completing a controlled skid test.
m. Note the coefficient of friction indicated by the sliding gauge indicator 80 on coefficient of friction graduations 85.

An incline correction factor must be applied to any coefficient of friction measurement taken on a grade or non-level road surface 100. The incline correction factor is added to or subtracted from the actual coefficient of friction reading taken from the friction measuring device 5, depending on whether the grade is uphill or downhill. The incline correction factor is added for an upgrade road surface 100. The incline correction factor is subtracted for a downgrade road surface 100. The incline correction factor is linearly proportional to the percent grade of the road surface 100. The exact slope of this mathematical relationship has been determined through calibration. Applicant has determined this equation and slope from many of testing their calibration plates 110 on various uphill and downhill inclines, with various coefficient of friction measuring devices, to precisely determine the slope of the incline correction factor as related to percent incline. Applicant uses this linear equation to determine the incline correction factor. If the road surface is level, the incline correction factor is zero. If the road surface has a percent grade of 0.5, the incline correction factor is about 0.025.

Consequently, the procedure to use pneumatic ram road surface coefficient of friction measuring device 5 in order to measure the coefficient of friction of a road surface 100 may further comprises the following steps.
n. Measure the incline of the road surface being tested as a percent grade from exactly horizontal.
o. Enter the incline measurement into a mathematical equation to solve for an incline correction factor.
p. Add this incline correction factor to the coefficient of friction indicated by the sliding gauge indicator 80 on coefficient of friction graduations 85 if the incline is an upgrade.
q. Subtract this incline correction factor from the coefficient of friction indicated by the sliding gauge indicator 80 on coefficient of friction graduations 85 if the incline is a downgrade.
r. Note the coefficient of friction result obtained.

Alternately, the procedure to use pneumatic ram road surface coefficient of friction measuring device 5 in order to measure the coefficient of friction of a road surface 100 comprises the following steps.
a. Position pneumatic ram road surface coefficient of friction measuring device 5 on a road surface 100 so that testing tire 10 is positioned above the position on the road surface 100 that requires measuring.
b. Secure pneumatic ram road surface coefficient of friction measuring device 5 from any movement relative to road surface 100.
c. Engage jack mechanism 40 to place pneumatic ram road surface coefficient of friction measuring device 5 into the upper position.
d. Pull the carriage plate 20 to its rear most position, with its rear surface resting against the front surface of rear rail plate 34.
e. Set sliding gage indicator 80 to the zero position that is the rear most position, with its rear edge resting against the front surface of front rail plate 30.
f. Cover or wet the full circumference of the testing tire 10 with glycerin.
g. Cover or wet with glycerin the entire section of road surface 100 corresponding to the skid path that testing tire 10 will take during a controlled skid test.
h. Rotate motor mounting arm 65 so that motor 60 comes into contact with testing tire 10.
i. Start motor 60 to cause the rotation of testing tire 10.
j. Stop motor 60 when the rotation of testing tire 10 reaches a first designated rotations per minute rate, which is greater than a second designated rotations per minute rate.
k. Rotate motor mounting arm 65 so that motor 60 comes out of contact with testing tire 10.
l. Allow the test tire 10 to decrease its rotations per minute rate due to friction to the second designated rotations per minute rate. (In best mode, second designated rotations per minute rate is 1050 RPM.)
m. Release jack mechanism 40 to drop pneumatic ram road surface coefficient of friction measuring device 5 to the lower position, thereby dropping the rotating testing tire 10 onto road surface 100 with testing tire 10 rotating at the second designated rotations per minute rate.
n. Allow testing tire 10 to skid along the road surface 100 until testing tire 10 comes to rest, thereby completing a controlled skid test.
o. Note the coefficient of friction indicated by the sliding gauge indicator 80 on coefficient of friction graduations 85.

An incline correction factor must be applied to any coefficient of friction measurement taken on a grade or non-level road surface 100. The incline correction factor is added to or subtracted from the actual coefficient of friction reading taken from the friction measuring device 5, depending on whether the grade is uphill or downhill. The incline correction factor is added for an upgrade road surface 100. The incline correction factor is subtracted for a downgrade road surface 100. The incline correction factor is linearly proportional to the percent grade of the road surface 100. The exact slope of this mathematical relationship has been determined through calibration. Applicant has determined this equation and slope from many of testing their calibration plates 110 on various uphill and downhill inclines, with various coefficient of friction measuring devices, to precisely determine the slope of the incline correction factor as related to percent incline. Applicant uses this linear equation to determine the incline correction factor. If the road surface is level, the incline correction factor is zero. If the road surface has a percent grade of 0.5, the incline correction factor is about 0.025.

Consequently, the procedure to use pneumatic ram road surface coefficient of friction measuring device 5 in order to measure the coefficient of friction of a road surface 100 may further comprises the following steps.

p. Measure the incline of the road surface being tested as a percent grade from exactly horizontal.
q. Enter the incline measurement into a mathematical equation to solve for an incline correction factor.
r. Add this incline correction factor to the coefficient of friction indicated by the sliding gauge indicator 80 on coefficient of friction graduations 85 if the incline is an upgrade.
s. Subtract this incline correction factor from the coefficient of friction indicated by the sliding gauge indicator 80 on coefficient of friction graduations 85 if the incline is a downgrade.
t. Note the coefficient of friction result obtained.

What is claimed is:

1. A pneumatic ram road surface coefficient of friction measuring device comprising:
    a testing tire mounted on a wheel that is rigidly attached to an axle;
    a carriage plate that is a rigid rectangular cuboid member with a top surface, a bottom surface, a left surface, a right surface, a front surface and a rear surface;
    a left rail that is a rigid oblong member with a longitudinal axis, a front end, and a rear end;
    a right rail that is a rigid oblong member with a longitudinal axis, a front end, and a rear end;
    a front rail plate that is a rigid rectangular cuboid member with a front, rear, top, bottom, left, and right surface;
    a rear rail plate that is a rigid rectangular cuboid member with a front, rear, top, bottom, left, and right surface; and
    at least one pneumatic ram, comprising a rod member with a front end and a rear end, a piston member with a front end and a rear end, and a cylinder member with a hollow interior, a front end, and a rear end, wherein,
    said axle is pivotally attached to said carriage plate,
    said left rail is positioned adjacent to and parallel with said left surface of said carriage plate,
    said right rail is positioned adjacent to and parallel with said right surface of said carriage plate,
    said front end of said right rail is rigidly attached to said rear surface of said front rail plate, perpendicular thereto,
    said rear end of said right rail is rigidly attached to said front surface of said rear rail plate, perpendicular thereto,
    said front end of said left rail is rigidly attached to said rear surface of said front rail plate, perpendicular thereto,
    said rear end of said left rail is rigidly attached to said front surface of said rear rail plate, perpendicular thereto,
    said carriage plate is slideable attached to said left rail with said left surface of said carriage plate parallel with said longitudinal axis of said left rail,
    said carriage plate is slideable attached to said right rail with said right surface of said carriage plate parallel with said longitudinal axis of said right rail,
    said rear end of said rod member is attached to said front surface of said rear rail plate,
    said front end of said rod member is attached to said rear end of said piston member,
    said piston member is slideable attached inside said hollow interior of said cylinder member, and
    said front end of said cylinder member is attached to said carriage plate.

2. A pneumatic ram road surface coefficient of friction measuring device as recited in claim 1 further comprising:

a front caster plate that is a rigid horizontal rectangular cuboid member with a front, rear, top, bottom, left, and right surface;
a rear caster plate that is a rigid horizontal rectangular cuboid member with a front, rear, top, bottom, left, and right surface; and
a jack mechanism with a top end and a bottom end; wherein,
said bottom surface of said front rail plate is rigidly attached to said top surface of said front caster plate,
said rear surface or said bottom surface of said rear rail plate is rigidly attached to said top end of said jack mechanism,
said bottom end of said jack mechanism is attached to or supported by said top surface of said rear caster plate,
said jack mechanism is a means to lift and hold said rear rail plate, in an upper position, above said rear caster plate, to create a gap between the top surface of said rear caster plate and the bottom surface of said rear rail plate, and
said jack mechanism is also a means to release or drop said rear rail plate, from said upper position, to allow said rear rail plate to fall back down to a lower position, wherein said bottom surface of said rear rail plate contacts and rests on said top surface of said rear caster plate.

3. A pneumatic ram road surface coefficient of friction measuring device as recited in claim 2, wherein,
said front end of said cylinder member of said at least one pneumatic ram further comprises an air vent and
said rear end of said cylinder member of said at least one pneumatic ram further comprises a calibration valve that is an adjustable air valve.

4. A pneumatic ram road surface coefficient of friction measuring device as recited in claim 3 further comprising:
a sliding gauge indicator; and
a set of coefficient of friction graduations, wherein,
said sliding gauge indicator is a rigid member, with a front edge and a rear edge, slideably attached said left rail or said right rail,
said coefficient of friction graduations are markings on said left rail or said right rail 26, or, alternately, on a scale, a tape, or a ruler attached to said left rail or to said right rail.

5. A pneumatic ram road surface coefficient of friction measuring device as recited in claim 4 further comprising:
a motor; and
a motor mounting arm, wherein,
said motor mounting arm is rigid oblong horizontal member with a front end, a mid-section, and a rear end,
said motor is rigidly attached to said front end of said motor mounting arm, and
said mid-section of said motor mounting arm is pivotally attached to said top surface, said front surface, or said rear surface of said rear rail plate.

6. A process to use a pneumatic ram road surface coefficient of friction measuring device as recited in claim 5, comprising the following steps:
a. Position said pneumatic ram road surface coefficient of friction measuring device 5 on a road surface so that said testing tire is positioned above a position on said road surface that requires a coefficient of friction measurement;
b. Secure said pneumatic ram road surface coefficient of friction measuring device from any movement relative said road surface;
c. Engage said jack mechanism to place said pneumatic ram road surface coefficient of friction measuring device into said upper position;
d. Pull said carriage plate back to a rear most position, with said rear surface of said carriage plate resting against said front surface of said rear rail plate;
e. Pull said sliding gage indicator back to a rear most position, with said rear edge of said sliding gage indicator resting against said front surface of said front rail plate;
f. Rotate said motor mounting arm so that said motor comes into contact with said testing tire;
g. Start said motor to cause the rotation of said testing tire;
h. Stop said motor when said testing tire reaches a first designated rotations per minute rate, which is greater than a second designated rotations per minute rate;
i. Rotate said motor mounting arm so that said motor comes out of contact with said testing tire;
j. Allow said test tire to decrease its rotations per minute rate to said second designated rotations per minute rate;
k. Release said jack mechanism to drop said pneumatic ram road surface coefficient of friction measuring device to said lower position, thereby dropping testing tire onto said road surface with said testing tire rotating at said second designated rotations per minute rate;
l. Allow said testing tire to skid along said road surface until said testing tire comes to rest; and
m. Note a coefficient of friction indicated by said sliding gauge indicator on said coefficient of friction graduations.

7. A pneumatic ram road surface coefficient of friction measuring device as recited in claim 5 further comprising:
a calibration plate; and
a calibration plate holder, wherein,
said calibration plate is a rigid rectangular planar member with a top surface, a bottom surface, a left edge, a right edge, a front edge, a rear edge, and a longitudinal axis,
said top surface of said calibration plate has a plurality of vertical parallel ridges running from said left edge to said right edge,
said calibration plate holder is a rigid rectangular horizontal planar member with a top surface, a bottom surface, a left edge, a right edge, front edge, a rear edge, and a mounting hole,
said mounting hole in said calibration plate is a rectangular shaped void with a longitudinal axis parallel with said longitudinal axis of said calibration plate holder.

8. A process to calibrate a pneumatic ram road surface coefficient of friction measuring device as recited in claim 7 comprising the following steps:
a. Position said calibration plate holder on a level surface and secure thereto;
b. Mount said calibration plate into said mounting hole on said calibration plate holder;
c. Engage said jack mechanism to place said pneumatic ram road surface coefficient of friction measuring device into said upper position;
d. Pull said carriage plate back to a rear most position, with said rear surface of said carriage plate resting against said front surface of said rear rail plate;
e. Position said pneumatic ram road surface coefficient of friction measuring device on top of said calibration plate holder with said longitudinal axes of said left rail and said right rail parallel with said longitudinal axis of said calibration plate holder, with said testing tire positioned directly above said calibration plate and adjacent to said rear edge of said calibration plate;
f. Pull said sliding gage indicator back to a rear most position, with said rear edge of said sliding gage indicator resting against said front surface of said front rail plate;
g. Rotate said motor mounting arm so that said motor comes into contact with said testing tire;
h. Start said motor to cause the rotation of said motor and said testing tire;
i. Stop said motor when said testing tire reaches a first said designated rotations per minute rate, which is greater than a second designated rotations per minute rate;
j. Rotate said motor mounting arm so that said motor comes out of contact with said testing tire;
k. Allow said test tire to decrease its rotations per minute rate to said second designated rotations per minute rate;
l. Release said jack mechanism to drop said pneumatic ram road surface coefficient of friction measuring device to said lower position, thereby dropping said testing tire onto said upper surface of said calibration plate with said testing tire rotating at said second designated rotations per minute rate;
m. Allow said testing tire to skid along said upper surface of said calibration plate until said testing tire comes to rest;
n. Note a coefficient of friction measurement indicated by said sliding gauge indicator on said coefficient of friction graduations;
o. Compare said coefficient of friction measurement with a known coefficient of friction measurement of said calibration plate;
p. If said coefficient of friction measurement is greater than said known coefficient of friction of said calibration plate, partially close said calibration valve;
q. If said coefficient of friction measurement is less than said known coefficient of friction of said calibration plate, partially open said calibration valve; and
r. Repeat said steps c-q until said coefficient of friction measurement matches said known coefficient of friction of said calibration plate.

* * * * *